United States Patent
Bullock et al.

(10) Patent No.: US 9,905,769 B2
(45) Date of Patent: *Feb. 27, 2018

(54) PROCESS OF MANUFACTURING AN ELECTRON TRANSPORT MATERIAL

(71) Applicant: PHILLIPS 66 COMPANY, Houston, TX (US)

(72) Inventors: Joseph Bullock, Bartlesville, OK (US); Brian Worfolk, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/245,939

(22) Filed: Aug. 24, 2016

(65) Prior Publication Data

US 2017/0098772 A1 Apr. 6, 2017

Related U.S. Application Data

(60) Provisional application No. 62/235,875, filed on Oct. 1, 2015.

(51) Int. Cl.
| | |
|---|---|
| *C07C 69/76* | (2006.01) |
| *H01L 51/00* | (2006.01) |
| *C07C 213/02* | (2006.01) |
| *C07C 213/08* | (2006.01) |
| *C07C 219/10* | (2006.01) |
| *H01L 51/42* | (2006.01) |

(52) U.S. Cl.
CPC ........ *H01L 51/0047* (2013.01); *C07C 213/02* (2013.01); *C07C 213/08* (2013.01); *C07C 219/10* (2013.01); *H01L 51/0003* (2013.01); *C07C 2604/00* (2017.05); *H01L 51/4253* (2013.01)

(58) Field of Classification Search
CPC ............. H01L 51/0047; H01L 51/4253; C07C 213/02; C07C 213/08; C07C 219/10; C07C 2104/00
See application file for complete search history.

(56) References Cited

U.S. PATENT DOCUMENTS

| | | | |
|---|---|---|---|
| 6,368,732 B1 | 4/2002 | Jin et al. | |
| 6,812,399 B2 | 11/2004 | Shaheen et al. | |
| 6,858,161 B2 | 2/2005 | Abe et al. | |
| 7,183,418 B2 | 2/2007 | Heeney et al. | |
| 7,332,223 B2 | 2/2008 | Sotzing et al. | |
| 7,507,351 B2 | 3/2009 | Tsuda et al. | |
| 7,524,922 B2 | 4/2009 | Heeney et al. | |
| 7,928,237 B2 | 4/2011 | Clark et al. | |
| 8,242,235 B2 | 8/2012 | Tsuda et al. | |
| 8,247,803 B2 | 8/2012 | Choi et al. | |
| 8,309,755 B2 * | 11/2012 | Dunn .................... | C07C 213/06 560/217 |
| 8,367,798 B2 | 2/2013 | Yang et al. | |
| 8,372,945 B2 | 2/2013 | Hou et al. | |
| 8,436,134 B2 | 5/2013 | Yu et al. | |
| 8,653,228 B2 | 2/2014 | Yu et al. | |
| 8,703,960 B2 | 4/2014 | Huang | |
| 8,895,751 B2 | 11/2014 | Huang | |
| 8,968,885 B2 | 3/2015 | Brown et al. | |
| 2003/0194630 A1 | 10/2003 | Beck et al. | |
| 2005/0082525 A1 | 4/2005 | Heeney et al. | |
| 2005/0176684 A1 | 8/2005 | Bookser et al. | |
| 2005/0209419 A1 | 9/2005 | Zahn et al. | |
| 2006/0071200 A1 | 4/2006 | Nordquist et al. | |
| 2006/0223977 A1 | 10/2006 | Zahn et al. | |
| 2008/0103286 A1 | 5/2008 | Ong et al. | |
| 2009/0159120 A1 | 6/2009 | Wang et al. | |
| 2009/0159131 A1 | 6/2009 | Zheng et al. | |
| 2009/0159999 A1 | 6/2009 | Zheng et al. | |
| 2010/0006148 A1 | 1/2010 | Zheng et al. | |
| 2010/0018581 A1 | 1/2010 | Shrotriya et al. | |
| 2010/0078074 A1 | 4/2010 | Yang et al. | |
| 2010/0101636 A1 | 4/2010 | Zheng et al. | |
| 2010/0137518 A1 | 6/2010 | Yang et al. | |
| 2010/0224832 A1 | 9/2010 | Jou et al. | |
| 2010/0276071 A1 | 11/2010 | Shrotriya et al. | |
| 2010/0300520 A1 | 12/2010 | Su et al. | |
| 2010/0326497 A1 | 12/2010 | Yang et al. | |
| 2011/0008926 A1 | 1/2011 | Irvin et al. | |
| 2011/0031875 A1 | 2/2011 | Jou et al. | |
| 2011/0086994 A1 | 4/2011 | Wigglesworth et al. | |
| 2011/0124822 A1 | 5/2011 | Yu et al. | |
| 2011/0147725 A1 | 6/2011 | Seshadri | |
| 2011/0204341 A1 | 8/2011 | Brown et al. | |
| 2012/0071617 A1 | 3/2012 | Dueggeli et al. | |
| 2012/0085992 A1 | 4/2012 | Beujuge et al. | |

(Continued)

OTHER PUBLICATIONS

Jiao et al. (Self n-doped [6,6]-phenyl-C61-butyric acid 2-((2-(trimethylammonium)ethyl)-(dimethyl)ammonium) ethyl ester diiodides as a cathode interlayer for inverted polymer solar cells, J. Mater. Chem. A, 2, pp. 14720-14728, published Jul. 8, 2014).*

*Primary Examiner* — Yevgeny Valenrod
*Assistant Examiner* — Blaine G Doletski
(74) *Attorney, Agent, or Firm* — Phillips 66 Company

(57) ABSTRACT

A process of dissolving [6,6]-phenyl-$C_{60}$-butyric-N-2-dimethylaminoethyl ester in a solvent to produce a first mixture. A reagent is added to the first mixture to produce a second mixture. The second mixture is then refluxed to produce [6,6]-phenyl-$C_{60}$-butyric-N-2-trimethylammonium ethyl ester iodide.

5 Claims, 5 Drawing Sheets

(56) References Cited

U.S. PATENT DOCUMENTS

| | | |
|---|---|---|
| 2012/0118368 A1 | 5/2012 | Huang et al. |
| 2012/0123058 A1 | 5/2012 | Ohno et al. |
| 2012/0232237 A1 | 9/2012 | Li et al. |
| 2012/0264906 A1 | 10/2012 | Marks et al. |
| 2013/0056071 A1 | 3/2013 | Palkar et al. |
| 2013/0214213 A1 | 8/2013 | Wang et al. |
| 2014/0151657 A1 | 6/2014 | Wang et al. |
| 2014/0221590 A1 | 8/2014 | Woody et al. |
| 2015/0136224 A1 | 5/2015 | Shi et al. |
| 2015/0210800 A1 | 7/2015 | Wang et al. |

\* cited by examiner

PROCESS OF MANUFACTURING AN ELECTRON TRANSPORT MATERIAL

CROSS-REFERENCE TO RELATED APPLICATIONS

This application is a Non-Provisional application which claims the benefit of and priority to U.S. Provisional Application Ser. No. 62/235,875 filed Oct. 1, 2015, entitled "Process of Manufacturing an Electron Transport Material," which is hereby incorporated by reference.

STATEMENT REGARDING FEDERALLY SPONSORED RESEARCH OR DEVELOPMENT

None.

FIELD OF THE INVENTION

This invention relates to a method of manufacturing an interfacial material used in organic bulk heterojunction devices.

BACKGROUND OF THE INVENTION

Solar energy using photovoltaic effect requires active semiconducting materials to convert light into electricity. Currently, solar cells based on silicon are the dominating technology due to their high conversion efficiency. Recently, solar cells based on organic materials showed interesting features, especially on the potential of low cost in materials and processing. Judging from the recent success in organic light emitting diodes based on a reverse effect of photovoltaic effect, organic solar cells are very promising.

Polymeric solar cells are promising approach to photovoltaic applications as they are cost-effective, flexible, lightweight and potentially disposable. [6,6]-phenyl-$C_{60}$-butyric acid-2-hydroxyethyl ester has been found to be capable of being used in organic photovoltaics, however it lacks in exhibiting high short-circuit current density and fill factor. There exists a need to produce a polar fullerene derivative yielding high photovoltaic performances by exhibiting higher short-circuit current density and fill factor.

BRIEF SUMMARY OF THE DISCLOSURE

A process of dissolving [6,6]-phenyl-$C_{60}$-butyric-N-2-dimethylaminoethyl ester in a solvent to produce a first mixture. A reagent is added to the first mixture to produce a second mixture. The second mixture is then refluxed to produce [6,6]-phenyl-$C_{60}$-butyric-N-2-trimethylammonium ethyl ester iodide.

An electron transport material is also taught comprising [6,6]-phenyl-$C_{60}$-butyric-N-2-trimethylammonium ethyl ester iodide.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

Figure 1:
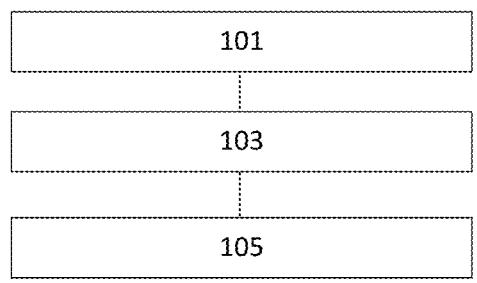
FIG. 1 depicts the process to produce [6,6]-phenyl-$C_{60}$-butyric-N-2-trimethylammonium ethyl ester iodide.

The present embodiment describes a process to produce [6,6]-phenyl-$C_{60}$-butyric-N-2-trimethylammonium ethyl ester iodide. As shown in FIG. 1, the process begins by dissolving [6,6]-phenyl-$C_{60}$-butyric-N-2-dimethylaminoethyl ester in a solvent to produce a first mixture, step 101. To the first mixture a reagent is added to produce a second mixture, step 103. The second mixture is then refluxed to produce [6,6]-phenyl-$C_{60}$-butyric-N-2-trimethylammonium ethyl ester iodide, step 105.

As described above step 101 begins by dissolving [6,6]-phenyl-$C_{60}$-butyric-N-2-dimethylaminoethyl in a solvent to produce a first mixture. Any conventionally known solvent capable of dissolving [6,6]-phenyl-$C_{60}$-butyric-N-2-dimethylaminoethyl can be used. In one example the solvent used can be any conventionally known solvent organic solvent. Examples of organic solvents can include dichlorobenzene, chlorobenzene, xylene, toluene, chloroform, tetrahydronaphthalene, carbon disulfide, dichloromethane, ethyl acetate, chloroform, ethanol, hexane, tetrahydrofuran, cyclohexane, and isopropanol. Any conventionally known method of dissolving

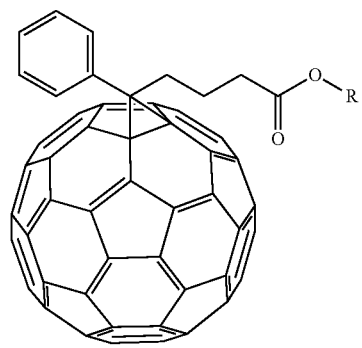

in the solvent can be used. These methods include mixing, stirring, heating and sonicating. The addition of the solvent is ideally done in an oxygen-free environment but not required.

In step 103, a reagent can be added to the first mixture to produce a second mixture. In one embodiment the reagent is iodomethane. In another embodiment, the use of any aliphatic iodide could be used. In another embodiment, dimethyl sulfate, methyl triflate, or dimethyl carbonate could be used.

In step 105, the second mixture is heated to a temperature of at least 50° C. to produce [6,6]-phenyl-$C_{60}$-butyric-N-2- trimethylammonium ethyl ester iodide. In an alternate embodiment the second mixture is heated to a temperature between 50° C. and 100° C. In one embodiment the second mixture is kept at this elevated temperature for at least 5 hours. In another embodiment the second mixture is kept at this elevated temperature for at least 18 hours.

In one embodiment the process of producing [6,6]-phenyl-$C_{60}$-butyric-N-2-dimethylaminoethyl ester for this process is produced from a process of dissolving [6,6]-phenyl-$C_{60}$-butyric acid methyl ester in 1,2-dichlorobenzene, under an oxygen free environment, to produce a first mixture. Dibutyltin(IV) oxide can then be added to the first mixture to produce a second mixture. To the second mixture 2-(dimethylamino)ethan-1-ol can be added to produce a third mixture. The third mixture can then be refluxed to produce a [6,6]-phenyl-$C_{60}$-butyric-N-2-dimethylaminoethyl ester.

The molar ratios of the chemical used can be.

| Chemical | Molar Ratio |
| --- | --- |
| [6,6]-phenyl-$C_{60}$-butyric-N-2-dimethylaminoethyl ester | 1 ± 0.9 |
| iodomethane | 200 ± 199 |

The following examples of certain embodiments of the invention are given. Each example is provided by way of explanation of the invention, one of many embodiments of the invention, and the following examples should not be read to limit, or define, the scope of the invention.

Example 1

[6,6]-Phenyl-$C_{60}$-butyric acid methyl ester (0.25 g, 0.274 mmol) was dissolved in 1,2-dichlorobenzene (12 mL) in a dry schlenk flask under argon. Dibutyltin(IV) oxide (0.014 g, 0.055 mmol) was added in one portion. 2-(Dimethylamino)ethan-1-ol (2 mL) was added in one portion and the solution heated to 150° C. for two hours. The solution was cooled and poured directly onto silica gel and eluted with toluene until all the 1,2-dichlorobenzene had flushed through. Then 6:1 toluene/triethylamine was eluted through to obtain pure product that was further purified by dissolving in chloroform (~4 mL) and allowing methanol to slowly diffuse into the solution to form brown crystals of [6,6]-phenyl-$C_{60}$-butyric-N-2-dimethylaminoethyl ester (0.293 g, 55% yield).

Example 2

[6,6]-phenyl-$C_{60}$-butyric-N-2-dimethylaminoethyl ester (0.05 g, 0.052 mmol) was dissolved in dry tetrahydrofuran (2 mL) in a dry sealable vessel under argon. Iodomethane (1.5 mL) was added in one portion and the vessel was sealed. The solution was heated to 60° C. for 18 hours. The solution was cooled and opened to allow all liquids to evaporate. The solid residue was suspended in methanol, diluted with acetone, and centrifuged. This process was repeated two more times to produce pure [6,6]-phenyl-$C_{60}$-butyric-N-2-trimethylammonium ethyl ester iodide as a metallic green powder.

NMR Spectroscopy

Nuclear magnetic resonance spectroscopy was performed on a 400 NMR spectrometer, operating at 400.16 MHz for $^1$H, and 100.04 MHz for $^{13}$C.

Figure 2:
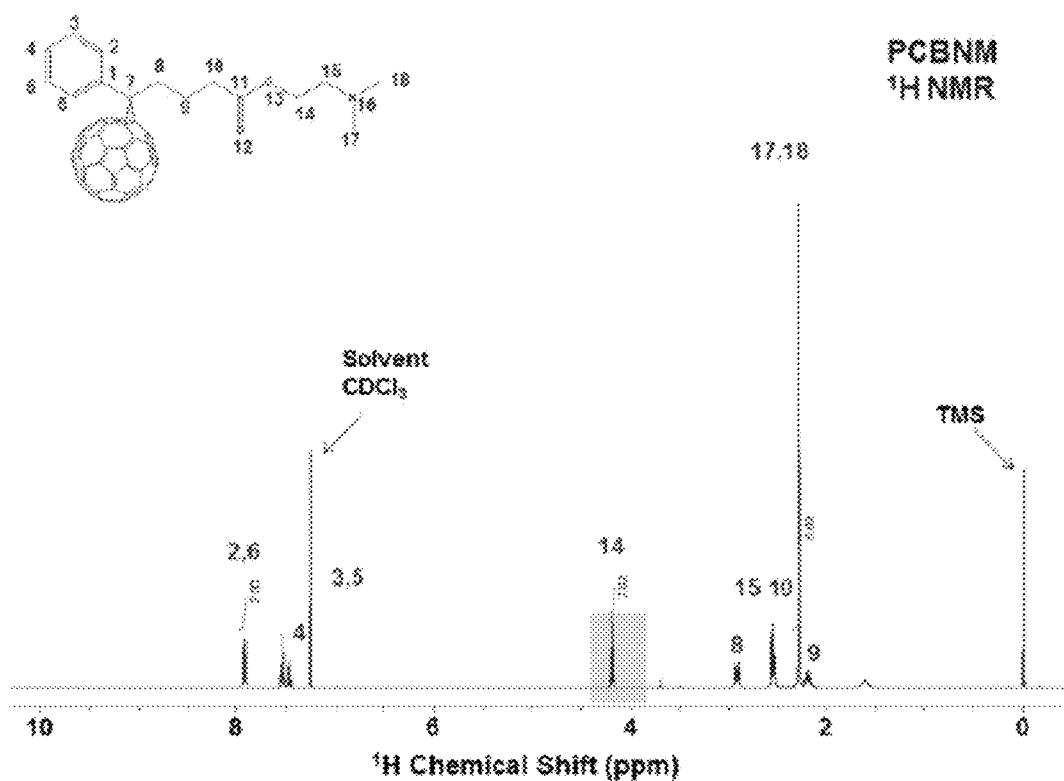
FIG. 2 depicts [6,6]-phenyl-$C_{60}$-butyric-N-2-dimethylaminoethyl ester at $^1$H NMR.

FIG. 2 depicts [6,6]-phenyl-$C_{60}$-butyric-N-2-dimethylaminoethyl ester at $^1$H NMR.

Figure 3:
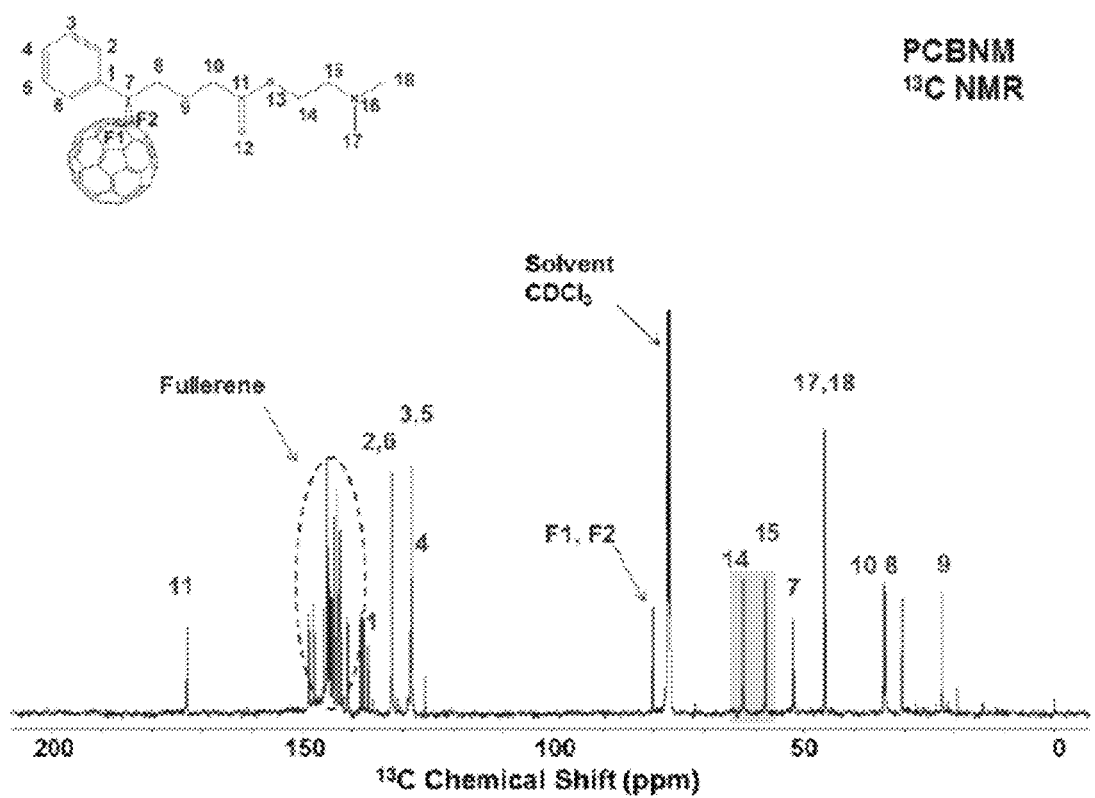
FIG. 3 depicts [6,6]-phenyl-$C_{60}$-butyric-N-2-dimethylaminoethyl ester at $^{13}$C NMR.

FIG. 3 depicts [6,6]-phenyl-$C_{60}$-butyric-N-2-dimethylaminoethyl ester at $^{13}$C NMR.

Figure 4:
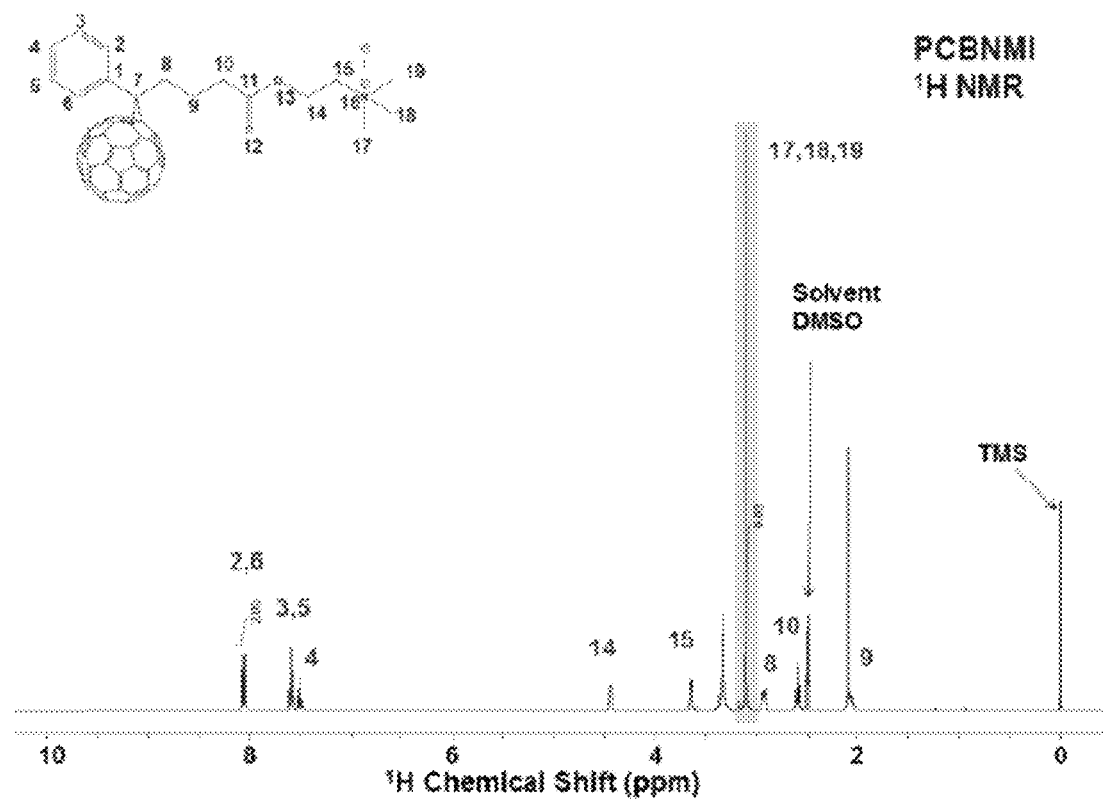
FIG. 4 depicts [6,6]-phenyl-$C_{60}$-butyric-N-2-trimethylammonium ethyl ester iodide at $^1$H NMR.

FIG. 4 depicts [6,6]-phenyl-$C_{60}$-butyric-N-2-trimethylammonium ethyl ester iodide at $^1$H NMR.

Figure 5:
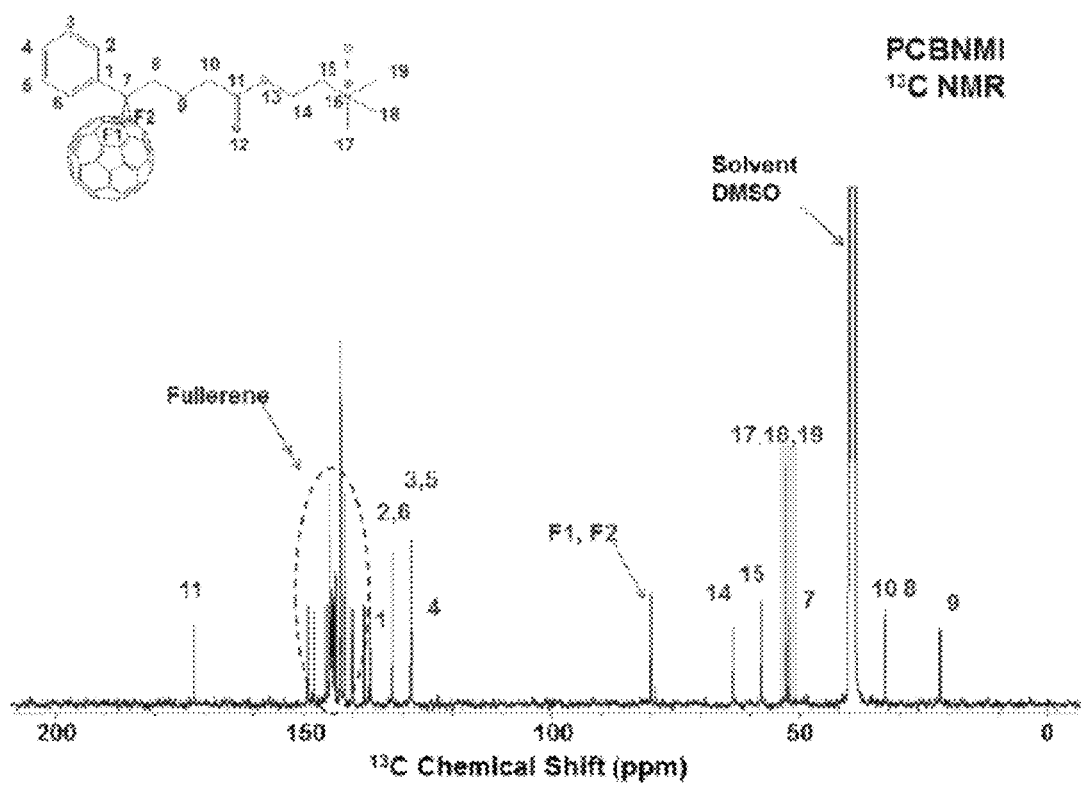
FIG. 5 depicts [6,6]-phenyl-$C_{60}$-butyric-N-2-trimethylammonium ethyl ester iodide at $^{13}$C NMR.

FIG. 5 depicts [6,6]-phenyl-$C_{60}$-butyric-N-2-trimethylammonium ethyl ester iodide at $^{13}$C NMR.

Performance Data

Average performance data of different organic photovoltaic devices using different electron transport layers were done.

| Electronic Transport layer | Open-circuit voltage Voc (V) | Short-circuit current density Jsc in mA/cm$^2$ | Fill Factor % | Power Conversion Efficiency % |
| --- | --- | --- | --- | --- |
| ZnO | 0.785 | 15.9 | 65.9 | 8.24 |
| ZnO:[6,6]-phenyl-$C_{60}$-butyric-N-2-dimethylaminoethyl ester | 0.765 | 16.2 | 59.9 | 7.47 |
| ZnO: [6,6]-phenyl-$C_{60}$-butyric-N-2-trimethylammonium ethyl ester iodide | 0.752 | 16.2 | 57.8 | 7.1 |

Work Function Data

Work function data of different electron transport layers were done.

| Material | Work Function (eV) |
| --- | --- |
| Indium Tin Oxide | 4.70 |
| ZnO | 3.75 |
| ZnO: [6,6]-phenyl-$C_{60}$-butyric-N-2-trimethylammonium ethyl ester iodide | 3.60 |

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:
1. A process comprising:
   a) dissolving [6,6]-phenyl-$C_{60}$-butyric-N-2-dimethylaminoethyl ester in a solvent to produce a first mixture;
   b) adding halomethanes, iodomethane, any aliphatic iodide, dimethyl sulfate, methyl triflate, or dimethyl carbonate to the first mixture to produce a second mixture;
   c) heating the second mixture to produce [6,6]-phenyl-$C_{60}$-butyric-N-2-trimethylammonium ethyl ester iodide, wherein [6,6]-phenyl-C60-butyric-N-2-dimethylaminoethyl ester is produced from:
d) dissolving [6,6]-phenyl-C60-butyric acid methyl ester in 1,2-dichlorobenzene, under an oxygen free environment, to produce a first mixture;
e) adding dibutyltin(IV) oxide to the first mixture to produce a second mixture;
f) adding 2-(dimethylamino)ethan-1-ol to the second mixture to produce a third mixture; and
g) refluxing the third mixture to produce [6,6]-phenyl-C60-butyric-N-2-dimethylaminoethyl ester.

2. The process of claim 1, wherein the solvent is an organic solvent.

3. The process of claim 1, wherein the solvent is selected from the group consisting of: dichlorobenzene, chlorobenzene, xylene, toluene, chloroform, tetrahydronaphthalene, carbon disulfide, dichloromethane, ethyl acetate, chloroform, ethanol, hexane, cyclohexane, tetrahydrofuran and isopropanol.

4. The process of claim 1, wherein the second mixture is heated to a temperature of at least 50° C.

5. The process of claim 1, wherein the second mixture is heated to a temperature between 50° C. and 100° C.

* * * * *